United States Patent [19]

Meserol et al.

[11] Patent Number: 5,427,739
[45] Date of Patent: Jun. 27, 1995

[54] APPARATUS FOR PERFORMING IMMUNOASSAYS

[75] Inventors: Peter M. Meserol, Montville; Rita C. Prodell, West Orange, both of N.J.

[73] Assignee: Schering-Plough Healthcare Products, Inc., Memphis, Tenn.

[21] Appl. No.: 275,935

[22] Filed: Jul. 15, 1994

Related U.S. Application Data

[63] Continuation of Ser. No. 936,697, Aug. 27, 1992, abandoned.

[51] Int. Cl.$^6$ ............................................. G01N 33/53
[52] U.S. Cl. ...................................... 422/58; 422/55; 422/56; 422/99; 422/102; 436/174; 436/177; 436/518; 436/519; 436/532; 436/535; 206/528; 210/445
[58] Field of Search ............... 422/55, 56, 58, 61, 422/99, 101, 102; 436/174, 177, 518, 519, 527, 531, 532, 535; 210/445, 451; 206/528, 532

[56] References Cited

U.S. PATENT DOCUMENTS

| | | | |
|---|---|---|---|
| 3,811,840 | 5/1974 | Bauer et al. | 23/253 |
| 3,888,629 | 6/1975 | Bagshawe | 23/230 |
| 4,466,740 | 8/1984 | Kano et al. | 356/246 |
| 4,477,575 | 10/1984 | Vogel et al. | 436/177 X |
| 4,623,461 | 11/1986 | Hossom et al. | 210/445 |
| 4,632,901 | 12/1986 | Valkirs et al. | 435/5 |
| 4,770,853 | 9/1988 | Bernstein | 422/58 |
| 4,857,453 | 8/1989 | Ullman et al. | 435/7 |
| 4,918,025 | 4/1990 | Grenner | 436/165 |
| 4,943,522 | 7/1990 | Eisinger | 435/7 |
| 4,946,601 | 8/1990 | Fiehler | 210/782 |
| 4,975,366 | 12/1990 | Sudo et al. | 435/7 |
| 4,981,786 | 1/1991 | Dafforn et al. | 435/7 |
| 5,006,464 | 4/1991 | Chu et al. | 435/7.1 |
| 5,006,474 | 4/1991 | Horstman et al. | 436/524 |
| 5,078,968 | 1/1992 | Nason | 422/58 |
| 5,084,005 | 1/1992 | Kachigian | 604/1 |
| 5,137,808 | 8/1992 | Ullman et al. | 435/7.9 |

OTHER PUBLICATIONS

Super Duo ® Test Kit brochure by Leeco Diagnostics, Inc., 24475 W. 10 Mile Road, Southfield, Michigan 48034 (no date Available).

Preview ® Serum/Urine-hCG Test Kit brochure by Leeco Diagnostics, Inc., 24475 W. 10 Mile Road, Southfield, Michigan 48034, Jul. 1989.

Preview ® Strep-A Test Kit brochure by Leeco Diagnostics, Inc., 24475 W. 10 Mile Road, Southfield, Michigan 48034, Nov. 1990.

*Primary Examiner*—James C. Housel
*Assistant Examiner*—Harold Y. Pyon
*Attorney, Agent, or Firm*—Eric S. Dicker; John J. Maitner; Robert A. Franks

[57] ABSTRACT

Apparatus for performing immunoassays which is essentially self-contained, requiring only the introduction of a sample and, at appropriate times, washing solution. The apparatus (10) includes: a fluid container (12) having a central platform area with a reaction area (30) which can contain a reactive agent; a sample receiving chamber (22) having a sample conduit (24) located above the porous medium; at least one openable reagent container (46); a conduit (28) for directing reagents onto the porous medium; an opening member (50) attached to the upper unit and positioned to contact and open reagent containers sequentially, by incremental relative rotation of the upper and base units; and a window (34) for viewing the reaction area. The apparatus can also include a sampler member (58) in the nature of a tampon for assays involving samples taken from body cavities.

21 Claims, 6 Drawing Sheets

APPARATUS FOR PERFORMING IMMUNOASSAYS

CROSS-REFERENCE TO RELATED APPLICATIONS

This application is a continuation of Ser. No. 936,697 filed on Aug. 27, 1992 and now abandoned.

INTRODUCTION TO THE INVENTION

The present invention relates to the detection of antibodies or antigens by immunoassay, and more particularly to apparatus for conducting immunoassays.

Immunoassays have, over the past twenty five years, become very useful methods for determining the presence and/or amount of numerous substances in biologically derived samples. The techniques utilize antibodies produced by the immune system of an organism in response to the presence of foreign substances (antigens) introduced into the organism. Antibodies so produced are normally very specific in their actions toward antigens, resulting in assay procedures which can be made quite free of interferences. To provide an indication of the presence of a material, an antibody or antigen can be labeled with a detectable radioactive substance or an enzyme which reacts with a substrate to produce a color change.

One variety of immunoassay which has become quite common in clinical analysis applications is called "ELISA," an acronym for "enzyme linked immunosorbent assay." This technique is used to determine the presence of either antigens or antibodies. To determine antibodies, an antigen is fixed to a surface, the unknown quantity of antibody is added and allowed to bind with the antigen, then another enzyme-conjugated antibody, capable of binding to the first antibody, is added and allowed to bind. After washing, the enzyme can be detected by its activity on an added substrate. Similarly, antigens are determined by fixing a suitable and body to a solid phase, allowing the sample antigen to bind to the antibody and then adding a second, enzyme-conjugated antibody for that antigen.

Initially, immunoassays were conducted using plastic tubes or microtitration plates having small wells therein, and the solid phase antibody or antigen was coated on the interior of the tube or surface of the plate. Samples and other reagents were introduced into the wells or tubes. As an alternative, it was discovered that the solid phase antibody or antigen could be bound to a bead or a small particle, and these were placed into tubes or the wells of a plate, thus localizing the area in which color changes take place. These procedures are still very widely used, particularly in large laboratories where numerous assays are performed each day.

Valkirs et al., in U.S. Pat. No. 4,632,901, describe an apparatus for conducting immunoassays in a more expedient manner than with microtitration plates or tubes. In this apparatus, an antibody is fixed on a porous member such as a membrane or filter, and absorbent material is placed below, and in contact with, the porous member. The absorbent material draws fluids through the porous member, facilitating rapid reactions without lengthy incubation times.

U.S. Pat. No. 5,006,464 to Chu et al. teaches a similar device, wherein a porous reaction membrane, having an immobilized receptor, is separated from a body of absorbent material by a septum. The septum is provided with discrete channels, which direct liquid flow preferentially toward or away from the center of the porous membrane.

It is now desired to provide an apparatus for conducting immunoassays, wherein the reagents and solid phases are contained within and are generally inaccessible to an operator. Such apparatus with greatly simplify the assay procedure and permit use by relatively untrained personnel, even by lay persons for home testing. It also would provide a greater convenience for laboratories which do not conduct numerous immunoassays or numerous assays of a particular type, and wish to minimize equipment and reagent inventory; such laboratories are frequently found in physicians offices.

SUMMARY OF THE INVENTION

The present invention comprises apparatus for performing immunoassays, including a fluid container having a central platform area; a reaction area, in one embodiment having a bound antibody or antigen, located on the platform; a sample receiving chamber located above the porous medium; one or more reagent containers; a conduit for directing reagents from opened containers onto the porous medium; a member which can be positioned to contact the reagent container, for opening purposes; and a window for viewing the underside of the platform.

Preferably, the apparatus is self-contained, requiring only the introduction of a sample and, if necessary, washing solution between reagent additions. In a presently preferred embodiment, the apparatus is constructed in two independently rotatable sections, so that reagents can be added by merely rotating one section with respect to the other to accomplish opening of a reagent container.

For sampling from body surfaces or cavities, certain embodiments of the apparatus also include a tampon-like sampler made of a porous polymer, the sampler being sized for introduction into the sample receiving chamber. In other embodiments, a component similar in shape to the sampler can be used to filter liquid samples.

DETAILED DESCRIPTION OF THE INVENTION

The present invention is an apparatus for conducting immunoassays. Immunoassays, although currently used primarily for samples of biological origin, are at least theoretically applicable to the assay of any chemical compound. To test for the presence of a specific compound, only a specific antibody is needed, and these are either available commercially or can be readily produced in animals using very well known techniques. Immunoassays are commonly used at present to determine the presence of microorganisms of all types, including bacteria, viruses, fungi, mycoplasmas, protozoa and the like, as well as biochemically active substances such as immunoglobulins, hormones, drugs, toxins and the like. Further, methods have been published for determining pesticides and other chemical species in extracts of plant tissues or soil, and in biological specimens such as blood and urine. The present apparatus can be utilized for any of these procedures.

Figure 1:
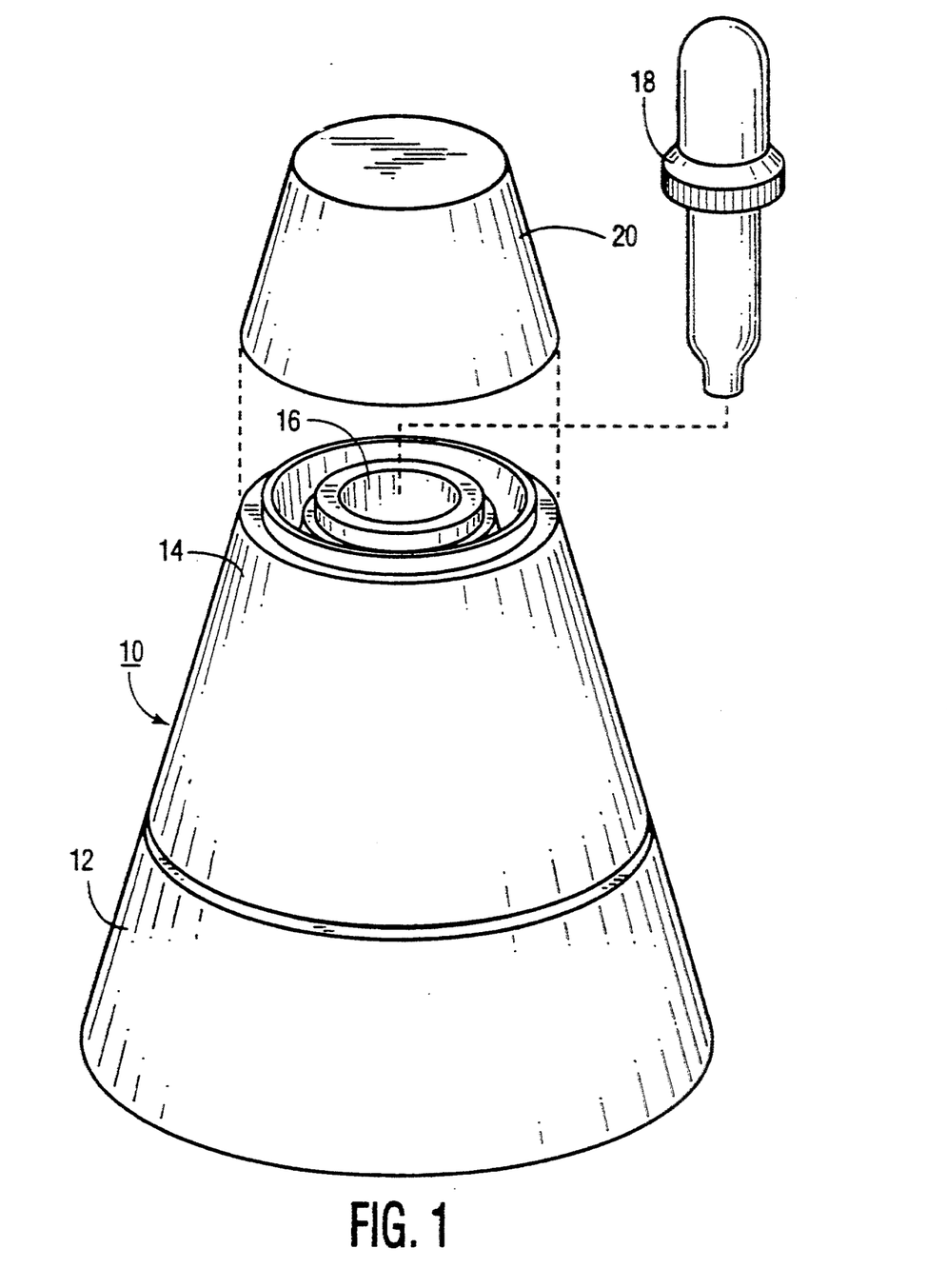
FIG. 1 is a sketch of the exterior of an apparatus for performing immunoassays, showing components which would be visible to the user.

Referring now to FIG. 1 of the drawings, there is shown an exterior view of a representative apparatus according to the present invention. In the drawing, assay apparatus 10 comprises a base unit 12 with superposed upper unit 14. The base unit and upper unit are connected so as to prevent longitudinal movement apart, to maintain a sealing relationship for containing any materials introduced into the interior of the apparatus, but are capable of relative rotation about a vertical axis through the center of the apparatus. The upper unit is provided with opening 16 for introduction of a sample. Container 18, which can be a common dropper device, is provided prefilled with solution (such as a buffer) for washing samples into the apparatus. For some assays, it is preferred that the dropper seals into opening 16, so that positive pressure may be established in the sample area by expelling liquids or air from the dropper. The apparatus is usually, but not always, provided with cover 20, which also can serve as a container for measuring and introducing a washing solution, such as water. The cover also can serve to seal the apparatus after introduction of all needed materials thereinto, to protect the user against contact with any potentially hazardous materials inside the apparatus.

Figure 2:
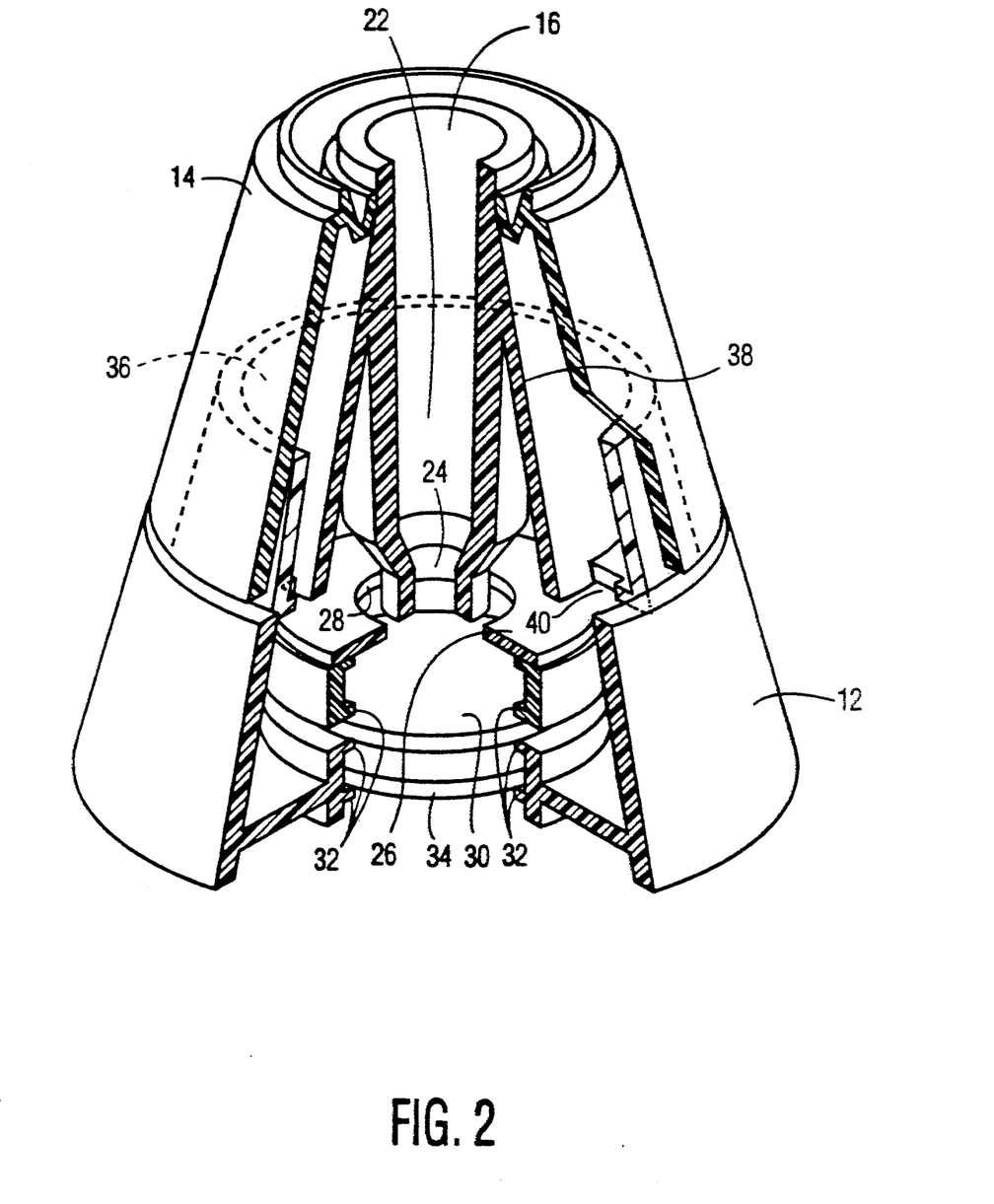
FIG. 2 is a cross-sectional diagram, showing the internal construction of the shell of the apparatus.

FIG. 2 shows a presently preferred internal structure of the assay apparatus. As shown in this figure, most of the functional elements of the apparatus are a part of base unit 12, upper unit 14 serving primarily as a cover for the internal features of the apparatus. The base unit comprises opening 16, the extension thereof forming sample receiving chamber 22. The sample receiving chamber is provided with sample conduit 24 at its lower terminus, centrally located in the apparatus. Funnel 26 is provided beneath the sample conduit, sloping generally downward toward central opening 28 to direct fluid flow into this opening. This opening is preferably somewhat larger in diameter than the diameter of sample conduit 24, such that fluid from the sample receiving chamber will normally fall directly through opening 28 and not contact the funnel.

Reaction area 30 is disposed beneath the funnel, such that fluids passing through central opening 28 will fall onto the reaction area. Positioning of the reaction area is maintained by a plurality of retainers 32 at the periphery of the reaction area, the reaction area forming a platform. These retainers can comprise clips which firmly grasp materials which form the reaction area.

The reaction area in one embodiment is a porous medium, and in another embodiment (as will be further explained in the examples) can be a transparent or translucent polymer having concentric grooves. The porous medium is preferably non-oriented and hydrophilic, so that fluids will flow by capillary or other action from the center to the periphery. Suitable materials for constructing the porous medium include cellulose fibers, glass fibers, polymeric fibers, polymer sheets, glass or polymer beads, glass frit and the like. Materials which are not normally hydrophilic can be treated with appropriate agents known in the art to provide hydrophilic properties. The porous medium is treated so as to bind antigen or antibody thereto, as will be discussed later.

Disposed beneath the reaction area is window 34, fabricated from a transparent or translucent material for viewing color changes which occur in the reaction area. The window is maintained in its position by a plurality of retainers 32. Although the window is shown in spaced relationship to reaction area 30, the window can serve as a platform for supporting a porous medium and no space would be required. For performing quantitative or semi-quantitative assays, the window can be provided with a color scale for comparing with colors generated by reactions on the reaction area. This window may not be required when the reaction area is a transparent or translucent polymer.

The base unit is further provided with upper wall 36, which is overlapped by the lower portion of upper unit 14. By providing a circumferential groove in the upper wall (not shown) and a projection (not shown) on the interior of the overlapping portion of upper unit 14, a snap fit can be obtained for retention of alignment between these components. Such arrangement will also permit relative rotation, the function of such rotation being explained later. Alternative locking arrangements between base unit 12 and upper unit 14 will be readily apparent to those having skill in the art.

Base unit 12 is also provided with support member 38 and a plurality of peripheral openings 40, the functions of these components becoming clear from the discussion which follows.

Figure 3:
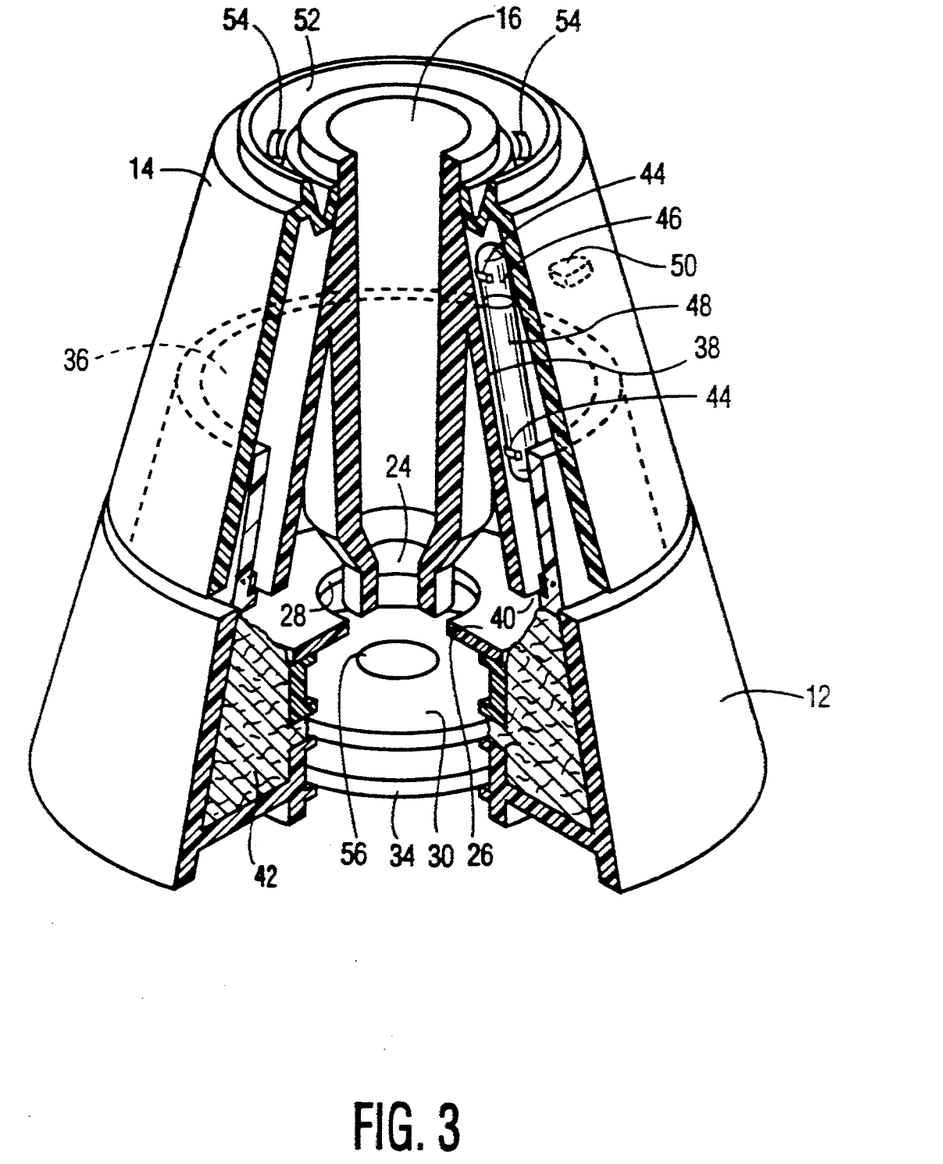
FIG. 3 is the cross-sectional view of FIG. 2, showing the addition of certain internal components.

Referring now to FIG. 3 of the drawings, there are shown additional features to the structure of FIG. 2. Base unit 12 is further provided with a quantity of absorbent material (not shown), located in annular cavity 42. Sufficient material should be provided to at least absorb all fluids which are to be directed onto reaction area 30. This absorbent material will preferably be in contact with the reaction area over a substantial portion of the reaction area circumference, to assist in transporting fluids away from the reaction area. Further, by retaining the fluids, the absorbent material will prevent reagents and other fluids which have previously been transported away from the reaction area from returning thereto.

Attached to support member 38, by means of clips 44, is at least one reagent container 46. The reagent container in the drawing is shown containing reagent 48, in an appropriate amount for the particular assay to be performed. The number of reagent containers provided depends upon the requirements of the particular assay, as is well known to those skilled in the art.

Opening member 50 is attached to an inner surface of upper unit 14, and contacts the reagent container during relative rotation of the base unit and the upper unit. For reagent containers made of glass, simple impact is sufficient to cause breakage and release the reagent from its container. Alternatively, the reagent containers can be made of a polymeric substance, such as polyethylene, in which case the opening member should be a cutting blade for shearing off the lower termination of the container, or a puncturing needle for creating an opening in a lower portion of the container. Upon being opened, the reagent traverses peripheral openings 40 and falls onto funnel 26. The reagent then is directed to central opening 28, from which it falls to the center of reaction area 30. Trough 52, provided in upper unit 14 about opening 16 of the base unit, is provided with a plurality of trough openings 54, through which a washing solution can be introduced to insure that all of the reagent is flushed onto the reaction area and to wash excess reagent from the reaction area. In many cases it is convenient to use cover 20 (FIG. 1) to measure an appropriate amount of a washing solution.

Particularly when more than one reagent is to be added, it will be helpful to the operator to provide indexing marks (not shown) to the exterior of the apparatus. By using the marks to indicate proper rotational positioning, the operator will be aware of the particular reagent being dispensed at a given moment.

In FIG. 3, reaction area 30 is a porous medium, and binding area 56 is shown as a limited area. The binding area is the location of bound antibody or antigen (including happen), with which the substance to be detected by the assay can bind. For some assays, the binding area can be the entire porous medium, but for enhanced sensitivity, it may be desirable to concentrate the bound antibody or antigen in a small discrete area, or several small discrete areas, of the porous medium. When the discrete areas constitute an easily recognizable shape, positive test results may be more visible. Methods for immobilization of antibodies or antigens on solid surfaces are known in the art, and need not be discussed here. Methods are known for covalently attaching antibodies and antigens to cellulose and polyacrylamide, and by physical adsorption to plastics (including polystyrene, polyvinyl, polypropylene, and polycarbonate) and to silicone rubber or treated glass.

By immobilizing antibodies or antigens on a lower surface of the porous medium, the substance will not be washed off easily, and will remain more easily observed through the window.

It should be noted that more than one antibody and/or antigen can be bound to the porous medium, permitting simultaneous assays for multiple species with a single sample. Reagents for each assay can be incorporated into the apparatus, and discrete binding areas are observed for color changes specific to the assays.

Figure 4:
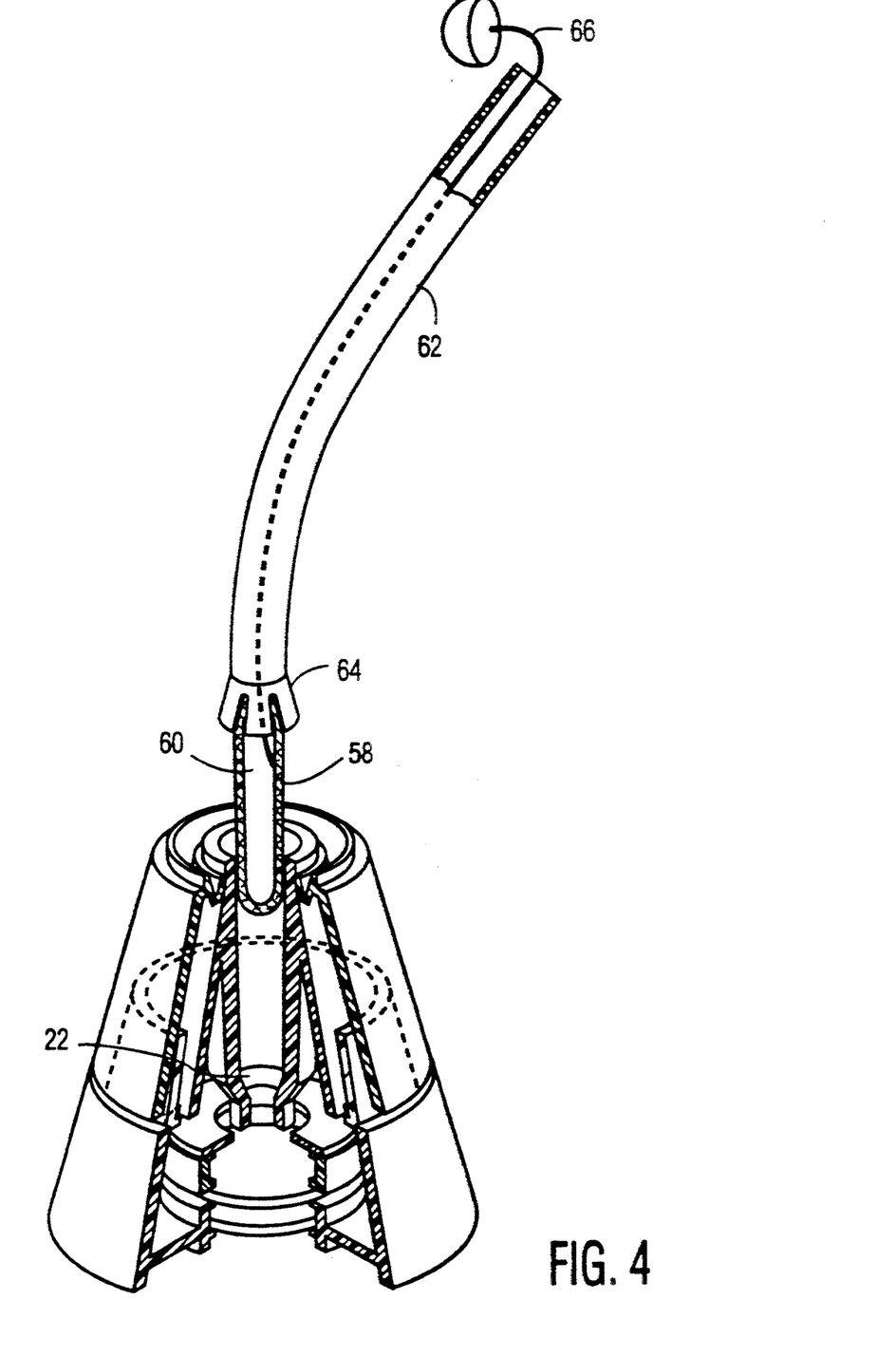
FIG. 4 shows a sample collecting tampon which can be used for certain assays with the apparatus.

FIG. 4 illustrates the use of a tampon-like sample collection system with the assay apparatus. Shown therein is sampler 58, connected to stem 62. The stem has a receptacle end 64, comprising flexible fingers which grip an inserted sampler. The sampler has a generally hollow interior 60 and, for sampling the interior of body cavities, has an attached cord 66 to permit removal should the sampler prematurely become detached from the stem. As shown in the figure, the sampler is sized to fit loosely inside sample receiving chamber 22 of the assay apparatus. After sample collection, the sampler may be detached from the stem by simply bending the unattached end of the stem downward, after the sampler has been inserted into the sample receiving chamber for a portion of its length. Thus, there will ordinarily be no necessity for touching the sampler after sampling.

Preferably, the sampler is formed from a porous polymeric substance having a large proportion of interconnected pores, more preferably from a sintered polyolefin. The POREX TM porous plastic, which is a sintered polyethylene sold by POREX Technologies Corporation, Fairburn, Ga., U.S.A., has been found quite suitable for use in the assay apparatus. Very little mucosal sample penetration into the interior of the sampler has been found to occur with the porous plastic. This permits essentially complete sample removal by introducing a washing solution to the interior of the sampler and applying a slight positive pressure; the washing solution tends to create a foam as it exits the outer surface of the sampler, and essentially quantitative sample removal from the sampler surface can be achieved. This is a particular advantage over the usual synthetic or cotton swabs commonly used for sample collection, which swabs entrain a large fraction of the sample; by removing essentially all of the sample from the sampling device, sensitivity of the method is increased and a more quantitative analysis can be obtained.

Figure 5:
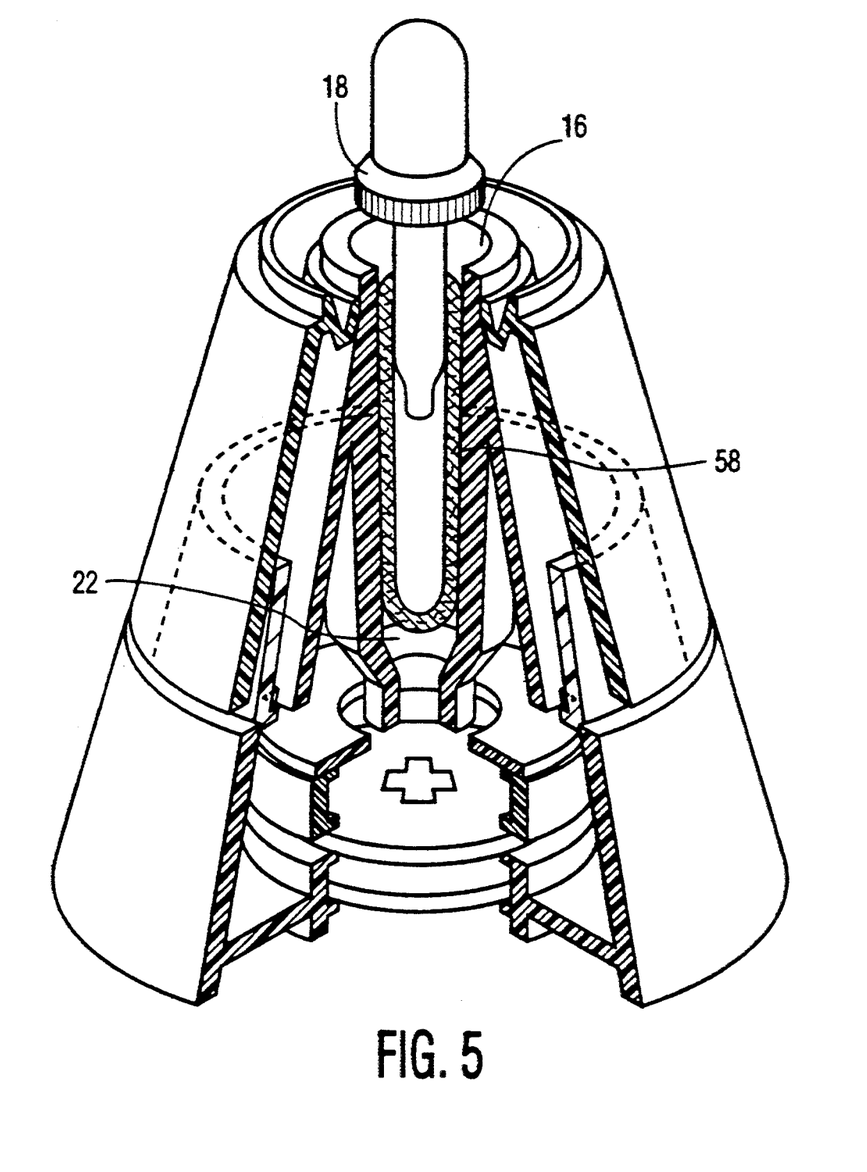
FIG. 5 is a cross-sectional diagram showing sample introduction into the apparatus, using the tampon.

FIG. 5 of the drawings shows the installation of sampler 58 into sample receiving chamber 22, and the insertion of container 18, holding a washing solution, into opening 16. Preferably, the container seals into the central opening of the sampler, so that ejecting liquids or air from the container will pressurize the sampler interior. By sizing the sampler slightly smaller than the interior of the sample receiving chamber, space will exist on the sides of the sampler for proper foaming to remove a maximum amount of the adhering sample.

Where it is desired to analyze samples of particulate-containing fluids requiring filtration, a tampon-like filtering member, shaped similarly to sampler 58, can be permanently mounted in sample receiving chamber 22. This filtering member can be formed from the sintered polymers previously described, or can be any of the usual cellulosic or synthetic filtration media known in the art. In some cases where pressurization is not needed, filtration of liquid samples can be more simply accomplished by placing a layer of filtration media at the bottom of the sample receiving area; this will also minimize the volume of media which can entrain a portion of the sample.

Figure 6:
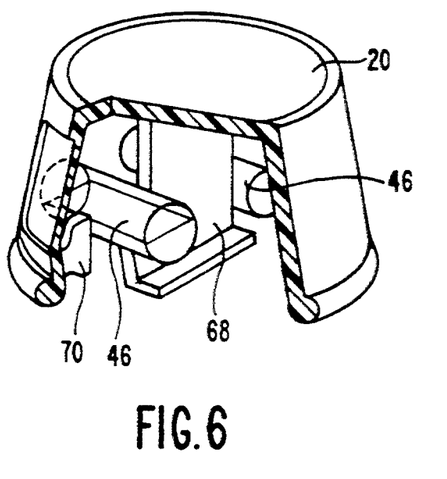
FIG. 6 is a partial cross-sectional view of a cover which can be used with the apparatus.

FIG. 6 shows an alternative embodiment for cover 20, for use when liquid samples are to be analyzed, and pre-treatment of a sample with one or more reagents is required before the sample is allowed to contact bound antibodies or antigens. The cover is fitted with a pedestal 68, preferably fabricated from a substantially rigid plastic material. This pedestal is adapted to retain one or more reagent containers 46, similar to those previously described. The pedestal shown in this drawing is adapted to hold up to two reagent containers, but could hold up to four containers if fabricated in a cruciform shape.

Preferably, the cover will be fabricated of a resilient polymeric material which retains a desired shape during standing, but can be readily temporarily deformed by squeezing with a person's fingers. One or more strikers 70 will be provided for each reagent container, and are attached to the interior wall of the cover. Squeezing the cover at an appropriate point will force a striker into a reagent container, thereby opening the container by breaking, cutting, etc., depending upon the nature of the container and striker. Upon opening of the container, its solid or liquid contents can be mixed with a sample contained within the cover by gently swirling the cover.

Different reagents can be added to the sample in a particular order, by sequentially squeezing different locations about the cover. The users will be aware of required mixing and/or standing periods between and after reagent additions, by instructions printed on the assay apparatus components or provided separately.

As is apparent to those skilled in the art, the concentrations and amounts of reagents used with the present invention will be dependent upon the dimensions of components in the apparatus, and the specific nature (e.g., absorption characteristics, and the like) of various components. Appropriate amounts and concentrations can be determined by routine experimentation, once an assay apparatus has been constructed. In many instances, it will be possible to simply utilize reagents which are commercially available, such as for immunoassays using conventional test tubes or microtitration plates.

The following examples illustrate various uses for the apparatus of the invention, and are not intended to limit the scope of the invention defined by the appended claims. In the examples, all percentages are expressed on a weight basis.

EXAMPLE 1

An apparatus is constructed for the detection of female genital tract infection by *Candida albicans*, i.e. vaginal candidiasis. This apparatus has, as reaction area 30 in FIG. 3, a transparent plastic disc having a concentric series of rings molded therein, said rings being of a size and spacing such that particles of various sizes can be classified (as in the particle agglutination analyzing plate of U.S. Pat. No. 4,466,740 to Kano et al., the disclosure of which is incorporated herein by this reference).

A vaginal swab sample is taken with the sampler collection system of FIG. 4, the sintered polyethylene sampler 58 is deposited into receptacle 22 of the assay apparatus, and stem 62 is removed.

The contents of pre-filled container 18 (FIG. 1), 2.0 milliliters of a saline solution containing 0.1% sodium azide and 3.0% glycine, are deposited into sampler interior 60. Saline solution is allowed to penetrate the porous walls of the sampler for about two minutes, then container 18 is sealed into the sampler interior and air in the container is expressed, forcing saline solution to the outer walls of the sampler and creating a foam, which strips the sample from the sampler and deposits it onto the reaction area. This foam, being quite unstable, becomes a liquid in a few minutes.

Upper unit 14 is rotated sufficiently to open a first reagent container, releasing 0.2 to 1 milliliters of a suspension of color dyed latex particles, coated with rabbit antibodies to *C. albicans*, in saline solution containing a glycine buffer, a protein stabilizer, and 0.1% sodium azide. The suspension flows onto reaction area 56, and is allowed to react with the sample for about three minutes; if antigens to *C. albicans* are present in the sample, the latex particles will agglutinate and settle to form a colored ring on the reaction area.

Upper unit 14 is further rotated to open a second reagent container, releasing 0.2 to 1 milliliters of a suspension of latex particles dyed a second color, the particles being coated with normal rabbit globulins, as a negative control. This reagent is allowed to react for about three minutes, and verifies proper response to the assay, by not agglutinating but forming a diffuse light color over a large area of the reaction area.

Finally, upper unit 14 is further rotated to open a third reagent container, releasing 2 milliliters of the same saline solution which was used to wash sample into the apparatus. This volume is chosen to cause the already substantially filled reaction area to overflow, bringing fluid into contact with absorbent material located in annular cavity 42. By means of a wicking action, the absorbent material will remove much of the fluid present on the reaction area, preventing flow of colored latex agglutinations as the apparatus is tilted for viewing the bottom of the reaction area.

A positive result is indicated by formation of a discrete colored area, caused by agglutination of the latex particles. If the sample did not contain sufficient *C. albicans* antigen, there should be no detectable agglutination and the latex particles will be dispersed over the reaction area.

EXAMPLE 2

The apparatus of the preceding example is constructed for the detection of *Trichomonas vaginalis* infections, by replacing the first reagent with a suspension of color dyed latex particles, coated by rabbit antibodies to *T. vaginalis*, using a similar saline solution.

Sample collection and assay procedures are as described in the preceding example.

EXAMPLE 3

The apparatus of Example 1 is constructed for the detection of female genital tract infections from *Candida albicans* and *Trichomonas vaginalis* in a single sample. To accomplish this modification, a fourth reagent container is provided to be opened after the first reagent container of the example, but before the second reagent container is opened. Further, the reaction area will be made somewhat larger to retain the increased total volume of reagents. This fourth reagent container contains the reagent of Example 2, wherein the latex particles are dyed a third color so as to be distinguishable from those having antibodies to *C. albicans* or normal rabbit globulins.

Operation of the apparatus is as described in Example 1, except that the fourth reagent container will be opened after the contents of the first reagent container have been allowed to react with the sample. After opening the fourth reagent container, a further period of about three minutes will be allowed for sample reaction, before proceeding to open the second reagent container.

The reagents and procedure for this assay are similar to those used in the test kit marketed by Leeco Diagnostics, Inc., Southfield, Mich. U.S.A. under the name SUPER DUO ®.

EXAMPLE 4

An apparatus is constructed for the detection of pregnancy, as shown by the presence of human chorionic gonadotropin (hCG) in urine samples. This apparatus is similar to that of Example 1, except that the reaction area is a porous medium having hCG antibody bound to the bottom surface. Absorbent material disposed in annular cavity 42 is placed in contact with edges of the reaction area. Only one reagent container is used, 0.2 to 1 milliliters of a substrate which can be acted upon by an enzyme to form a color (such as p-nitrophenyl phosphate, which forms a yellow p-nitrophenol with alkaline phosphatase). To conduct the assay, a sampler 58 (sized and having the proper porosity to hold one milliliter of sample in its pores) is immersed in a urine specimen and then placed into opening 16 of the apparatus. The contents of prefilled container 18 (0.5 milliliter of a conjugate of hCG antibody and alkaline phosphatase, in a 0.1% sodium azide solution) are deposited into sampler interior 60. Container 18 is then sealed into the opening of the sampler and, after allowing about two minutes for reaction of sample hCG with the conjugated antibody, air in the container is expressed to force antibody solution and the sample from the sampler, onto the reaction area.

After a five minute reaction period, excess (unbound) conjugated antibody is washed from the reaction area into the absorbent material by pouring about 10 milliliters of water into trough 52.

Rotation of upper unit 14 is then conducted to open the reagent container and, after a period of about three minutes, the bottom surface of the reaction area is inspected for color development which indicates the presence of hCG in the sample.

The reagents and procedure for this assay are similar to those used in the test kit marketed by Leeco Diagnostics, Inc., Southfield, Mich. U.S.A. under the name PREVIEW ® Serum/Urine-hCG.

EXAMPLE 5

An apparatus for detection of antigens from pharyngeal infection with Group A streptococci is constructed as in the preceding example, except that antibodies to the streptococci are bound to the underside of the reaction area. The cap of FIG. 6 is used, sized to hold about 30 milliliters of liquid and fitted with two reagent containers: one holds 1 milliliter of a mineral or organic acid, while the other holds 1 milliliter of a reducing agent. The reagent container in the apparatus body contains 0.5 milliliters of a substrate. Container 18 is prefilled with 0.5 milliliters of a conjugate of Group A streptococci antibody and an enzyme, in a 0.1% sodium azide solution.

To conduct an assay, a patient gargles for about ten seconds with 15 milliliters of isotonic saline and deposits the solution into cover 20. Using a squeezing finger pressure, both of the reagent containers in the cover are opened, and reagents are mixed with the sample by swirling. A period of about three minutes is allowed for extraction of antigen from the sample.

A portion of extracted sample is poured into sampler interior 60, to a pre-marked fill line (0.5 milliliter). The remainder of the sample is discarded. Contents of container 18 are added to the sampler interior, and five minutes are allowed to elapse for antigen-antibody binding. Container 18 is then sealed into the opening of the sampler, sample is forced from the sampler, and remaining steps from the preceding example are followed. Color development on the reaction area indicates the presence of Group A streptococci antigens.

The reagents and procedure for this assay are similar to those used in the test kit marketed by Leeco Diagnostics, Inc., Southfield, Mich. U.S.A. under the name PREVIEW ® Strep-A.

The assay apparatus of this invention is particularly useful for the diagnosis of infections, including infections by organisms including *Candida tropicalus, Candida glabrata* and the various organisms which infect the urinary tract. However, it also is useful for monitoring drug or hormonal presence in fluids such as urine and serum, and for determining the presence of toxins and other deleterious substances. Many other uses and embodiments will be apparent to those skilled in the art of immunoassays, and the scope of the invention as defined by the appended claims is not to be limited to the specific discussion and examples presented herein.

What is claimed is:

1. Apparatus for performing immunoassays, comprising:

(a) a base unit and a superposed upper unit, joined to permit relative rotation about a common central vertical axis;
    (b) fluid container means, having a central platform area, located in a lower portion of the base unit;
    (c) a reaction area containing an immobilized specific binding reagent on the platform area;
    (d) a window for viewing an underside of the reaction area;
    (e) a sample receiving chamber extending into upper portions of the upper unit, having a fluid outlet terminating above the reaction area;
    (f) at least one openable reagent container, attached to the base unit and positioned within the upper unit;
    (g) an opening member attached to the upper unit and positioned to contact and open reagent containers sequentially, by incremental relative rotation of the upper and base units; and
    (h) a conduit for directing fluid reagents from the reagent containers onto the reaction area.

2. The apparatus of claim 1, wherein the fluid container is provided with fluid absorbing material, disposed about the circumference of the platform.

3. The apparatus of claim 1, wherein the reaction area comprises a porous medium containing a reactive agent.

4. The apparatus of claim 3, wherein the porous medium comprises a non-oriented and hydrophilic material.

5. The apparatus of claim 3, wherein the porous medium comprises a polymeric material.

6. The apparatus of claim 3, wherein the porous medium is a cellulosic material.

7. The apparatus of claim 3, wherein the porous medium comprises a glass.

8. The apparatus of claim 3, wherein the reactive agent is an antibody.

9. The apparatus of claim 3, wherein the reactive agent is an antigen.

10. The apparatus of claim 3, wherein the reactive agent is present on a surface of the porous medium facing the window.

11. The apparatus of claim 3, wherein the porous medium contains more than one reactive agent.

12. The apparatus of claim 1, wherein the reaction area comprises a transparent or translucent polymer having concentric grooves.

13. The apparatus of claim 1, wherein the reagent container comprises a frangible material.

14. The apparatus of claim 1, wherein the reagent container comprises a polymeric material and the opening member comprises a cutting or puncturing device.

15. The apparatus of claim 1, wherein the window is provided with a color comparison chart.

16. The apparatus of claim 1, further comprising (i) a cover over the sample receiving chamber.

17. The apparatus of claim 1, further comprising (j) a container for introducing washing fluid into the sample receiving chamber.

18. The apparatus of claim 1, further comprising (k) a sampler for sample collection.

19. The apparatus of claim 18, wherein the sampler comprises a hollow porous polymer shape having a closed end.

20. The apparatus of claim 19, wherein the sampler comprises a porous sintered polymer.

21. The apparatus of claim 20, wherein the polymer is a polyolefin.

* * * * *